United States Patent [19]

Winchell et al.

[11] Patent Number: 5,409,689
[45] Date of Patent: Apr. 25, 1995

[54] MRI IMAGE ENHANCEMENT USING COMPLEXES OF PARAMAGNETIC CATIONS AND AMINE LIGANDS CONTAINING A MIXTURE OF PHOSPHONATE AND NON-PHOSPHONATE PENDANT ARMS

[75] Inventors: Harry S. Winchell, Lafayette, Calif.; Joseph Y. Klein, Haifa, Israel; Rosa L. Cyjon, Haifa, Israel; Eliot D. Simhon, Haifa, Israel

[73] Assignee: Concat, Ltd., Concord, Calif.

[21] Appl. No.: 106,764

[22] Filed: Aug. 13, 1993

[51] Int. Cl.⁶ ................... A61B 5/055; C07D 257/02
[52] U.S. Cl. ......................... 424/9; 436/173; 534/15; 534/16; 540/465; 540/474
[58] Field of Search ................ 424/9; 540/465, 474; 534/15, 16; 128/653.4, 654; 436/173

[56] References Cited

U.S. PATENT DOCUMENTS

| | | | |
|---|---|---|---|
| 4,429,124 | 1/1984 | Felix | 544/214 |
| 4,444,693 | 4/1984 | Felix | 260/502.5 |
| 4,515,766 | 5/1985 | Castronovo et al. | 424/1.1 |
| 4,647,447 | 3/1987 | Gries et al. | 424/9 |
| 4,693,884 | 9/1987 | Kleiner et al. | 424/1.1 |
| 4,749,560 | 6/1988 | Elgavish | 424/9 |
| 4,804,529 | 2/1989 | Bardy et al. | 424/9 |
| 4,880,007 | 11/1989 | Sadler et al. | 128/653.4 |
| 4,885,363 | 12/1989 | Tweedle et al. | 424/9 |
| 4,983,376 | 1/1991 | Sherry | 424/9 |
| 5,316,757 | 5/1994 | Sherry et al. | 424/9 |

FOREIGN PATENT DOCUMENTS

| | | |
|---|---|---|
| 0258616 | 3/1988 | European Pat. Off. . |
| 0275215 | 7/1988 | European Pat. Off. . |
| 0382582 | 8/1990 | European Pat. Off. . |
| 0404605 | 12/1990 | European Pat. Off. . |
| 0455380 | 6/1991 | European Pat. Off. . |
| 0468634 | 1/1992 | European Pat. Off. . |
| 1081169 | 3/1984 | U.S.S.R. . |
| 1098937 | 6/1984 | U.S.S.R. . |

OTHER PUBLICATIONS

Geraldes, C. F. G. C., et al., "Synthesis, Protonation Sequence, and NMR Studies of Polyazamacrocylic Methylenephosphonates," *Inorg. Chem.*, 28:3336-3341 (1989).

Sherry, A. D., et al., "Dy(DOTP)⁵⁻: A New, Stable ²³Na Shift Reagent," *J. Magnetic Resonance*, 76:528-533 (1988).

Gillard, R. D., et al, "Speciation in Aqueous Solutions of Di-Ethylenetriamine-N,N,N',N",N'" Pentamethylenephosphonic Acid and Some Metal Complexes," *Polyhedron*, 8(16):2077-2086 (1989).

Rizkalla, E. N., et al., "Nuclear Magnetic Resonance Study of Ethylenediaminetetrakis (methylenephosphonic acid) and Some Metal Complexes," *Inorganic Chemistry*, 22(10):1478-1482 (1983).

Polikarpov, Y. M., et al., "N,N',N"-Tris(phosphonomethyl)-1,4,7-triazacyclononane—a specific complexing agent for magnesium ion," *Izv. akad. Nauk SSSR, Ser. Khim.*, (7):1669-1670 (1982).

Kabachnik, M. I., et al., "Synthesis and Study of a New Complexon—N,N',N'-Tris(dihydroxyphosphorylmethyl)-1,4,7-triazacyclononane," *Izv. akad. Nauk SSSR, Ser. Khim.*, (4):835-843 (1984).

(List continued on next page.)

Primary Examiner—Gary E. Hollinden
Attorney, Agent, or Firm—Townsend and Townsend Khourie and Crew

[57] ABSTRACT

Ligands with three or more nitrogen atoms incorporated into a linear or cyclic backbone structure, with the nitrogen atoms substituted with a combination of phosphonate groups and nonphosphonate groups, of which at least two are phosphonate groups, are disclosed. These ligands are combined with paramagnetic metal cations and administered in the form of pharmacologically acceptable salts, are useful as MRI contrast enhancement agents, which tend to localize in bone tissue without being conjugated to bone-specific biomolecules. Triazacyclononanes and tetraazacyclododecanes, with dihydroxyphosphorylmethyl or dihydroxyphosphorylethyl groups linked to the backbone nitrogens are preferred.

65 Claims, No Drawings

OTHER PUBLICATIONS

Antipin, M. Y., et al., "Structure of the N,N',N"-Tris[-Dihydroxyphosphorylmethyl]-1,4,7-Triazacyclononane with an Enclosed Ferric Ion," *Dokl. Akad. Nauk SSSR*, 287(1):130–133 (Mar. 1986).

Geraldes, C. F. G. C., et al., "Evaluation of Polyaza Macrocyclic Methylene Phosphonate Chelates of $GD^{3+}$ Ions as MRI Contrast Agents," *Magnetic Resonance in Medicine*, 9:94–104 (1989).

Kabachnik, I. M., et al., "Synthesis and Acid-Base and Complex-Forming Properties of 1,4,7,10-Tetrakis(-Dihydroxyphosphorylmethyl)-1,4,7,10-Tetraazacyclododecane," *Izv. Akad. Nauk SSR, Ser. Khim.*, 4:844–849 (1984).

Geraldes, C. F. G. C., et al., "Synthesis, Protonation Sequence, and NMR Studies of Polyazamacrocyclic Methylenephosphonates," *Inorg. Chem.*, 28:3336–3341 (1989).

Polikarpov, Y. M., et al., "A new cyclopendant organophosphorus complexon: 1,4,7,10-tetrakis($\beta$-dihydroxyphosphorylethyl)-1,4,7,10-tetraazacyclododecane," *Chemical Abstracts*, 112:732 (1990).

Medved, T. Y., et al., "New cyclopendant organophosphorus complexons: 1,4,7-tris($\beta$-dihydroxyphosphorylethyl)-1,4,7-triazacyclononane," *Chemical Abstracts*, 111:784 (1989).

Buster, D. C., et al., "$TM(DOTP)^{5-}$: A $^{23}Na^{30}$ Shift Agent for Perfused Rat Hearts," *Magnetic Resonance in Medicine*, 15:25–32 (1990).

van Westrenen, J. et al., Bioconjugate Chemistry 3(6):524–532 (1992).

Tschudin, D et al., Helvetica Chimica Acta 71(1):100–106 (1988).

Kaken, T A et al., Pure & Applied Chemistry 61(5):879–883 (1989).

MRI IMAGE ENHANCEMENT USING COMPLEXES OF PARAMAGNETIC CATIONS AND AMINE LIGANDS CONTAINING A MIXTURE OF PHOSPHONATE AND NON-PHOSPHONATE PENDANT ARMS

This invention lies in the field of magnetic resonance imaging, and is relevant to the art of contrast enhancement agents used in connection with magnetic resonance imaging in medical diagnostics.

BACKGROUND OF THE INVENTION

The availability of magnetic resonance imaging (MRI) devices has led to the use of MRI in medical examinations for the detection and diagnosis of disease states and other internal abnormalities. The continued use and development of MRI has stimulated interest in the development of pharmaceutical agents capable of altering MRI images in diagnostically useful ways. Pharmaceutical agents (MRI pharmaceuticals) which are currently favored by researchers in the field are suitably complexed paramagnetic metal cations. The use of pharmaceuticals in MRI imaging offers major opportunities for improving the value of the diagnostic information which can be obtained.

Radiopharmaceuticals, which are used in radioisotopic imaging in a manner analogous to MRI pharmaceuticals, are a well developed field. The knowledge existing in this field thus provides a starting point for the development of MRI pharmaceuticals. MRI pharmaceuticals must meet certain characteristics, however, which are either not required or are considerably less critical in the case of radiopharmaceuticals. MRI pharmaceuticals must be used in greater quantities than radiopharmaceuticals. As a result, they must not only produce detectable changes in proton relaxation rates but they must also be (a) substantially less toxic, thereby permitting the use of greater amounts, (b) more water soluble to permit the administration of a higher dosage in physiologically acceptable volumes of solution, and (c) more stable in vivo than their radiopharmaceutical counterparts. In vivo stability is important in preventing the release of free paramagnetic metals and free ligand in the body of the patient, and is likewise more critical due to the higher quantities used. For the same reasons, MRI pharmaceuticals which exhibit whole body clearance within relatively short time periods are particularly desirable.

Since radiopharmaceuticals are administered in very small dosages, there has been little need to minimize the toxicity of these agents while maximizing water solubility, in vivo stability and whole body clearance. It is not surprising therefore that few of the ligands developed for use as components in radiopharmaceutical preparations are suitable for use in preparation of MRI pharmaceuticals. A notable exception is the well known ligand diethylene triamine pentaacefic acid (DTPA), which has proved useful in forming complexes with both radiocations, pharmacologically suitable salts of which provided useful radiopharmaceuticals, and paramagnetic cations such as gadolinium, whose pharmacologically suitable salts have proved useful as MRI pharmaceuticals.

Certain groups of radiopharmaceuticals tend to localize in bone tissue, and are thus of use in providing diagnostic information concerning bone disorders. The properties of these agents which lead to their localization in bone also allow for them to localize in soft tissues bearing recognitions features in common with bone. Thus, many radiopharmaceuticals which localize in bone are known, or believed, to localize in soft tissues which are found to have gross, microscopic or chemical evidence for deposition of calcium salts (e.g., metastatie calcification), such as might occur in association with tissue injury. Thus, radiopharmaceuticals have shown localization in rhabdomyolysis of various origins, in collagen disorders and in other injured tissues. Localization of such agents in areas of myocardial infarction is an example of one application which has proven diagnostically useful. Radiopharmaceuticals which localize in bone have also been shown to localize in normal and malignant breast tissue, in pleural effusions, in infarctions of the spleen and bowel, inflammatory bowel disease, radiation injury, metastatic calcification, and in a variety of malignant tumors, etc. Regardless of the mechanism of such localization we herein refer to the soft tissues which concentrate agents which localize in bone as "bearing recognition features in common with bone." Exclusive of their localization in bone and tissues bearing recognition features in common with bone, these agents generally are distributed in the extracellular fluid spaces of the body and therefore can be used to provide information concerning the content and kinetics of the extracellular fluid of normal and abnormal tissues. One example of the clinical utility of this behavior is the detection of disruption of the blood brain barrier wherein extracellularly distributed agents abnormally localize in the region of such disruption. Most of the presently known agents which localize in bone are excreted from the body by the kidneys and therefore can be used to evaluate the renal excretory system. It is possible that such agents could be made more lipophilic such that they would be excreted by the liver, and therefore could be used to evaluate the hepatobiliary excretory system.

Agents which localize in bone and which provide MRI contrast enhancement could be used to perform similar diagnostic procedures employing radiopharmaceuticals which localize in bone. Given the substantially greater spatial and temporal resolution of MRI techniques, as compared to nuclear medical techniques, it is anticipated that useful diagnostic information could be obtained in abnormalities which were not detected using nuclear medical techniques, as for example in detection of small areas of tissue damage and/or in small regions of deposition of calcium salts. Moreover, fixation of MRI contrast enhancement agents in such tissue would be expected to increase the relativity of the agent by decreasing the molecular rotation rate thereby increasing signal intensity. However, known radiopharmaceutical agents which localize in bone are retained in the region of their deposition for very prolonged periods of time making them unsuitable for use as MRI contrast agents. Moreover, these "bone seeking" pharmaceuticals which contain phosphonate groups are also known to be relatively strong chelators of calcium ions and their administration at the dose and dose rate levels associated with the use of MRI contrast agents can be associated with induction of acute hypocalcemia and attendant cardiac arrest.

Most known MRI pharmaceuticals when administered in vivo do not by themselves localize in specific tissues, but instead generally distribute in extracellular fluid space in a nonspecific manner. One means of achieving localization of these inherently nonspecific pharmaceuticals in selected tissues is by conjugation with biomolecules which localize in the region of interest. Another means is by incorporating the complexes into bodies which localize in the region of interest. Hormones, albumins, liposomes, and antibodies have been mentioned in such attachments or incorporation. See Giles, H., et al., U.S. Pat. No. 4,647,447, Mar. 3, 1987.

SUMMARY OF THE INVENTION

It has now been discovered that ligands containing amine groups plus a combination of phosphonate and non-phosphonate pendant arms, combined with paramagnetic metal cations and administered in the form of pharmacologically acceptable salts, offer preferential MRI image enhancement in bone tissue and other tissue bearing biospecific recognition features in common with bone. These complexes are fully suitable for use as MRI contrast enhancement agents, and tend to localize in bone tissue without either being conjugated to bone-specific biomolecules or being incorporated into bone localizing bodies. These agents further show near quantitative whole body clearance and possess all of the requirements of MRI contrast enhancement agents. The ligands contain a minimum of two phosphonate groups, preferably bonded through alkyl bridges to nitrogen atoms. Cyclic groups are still further preferred, notably polyazacycloalkanes. Particularly preferred ligands are triazaeyelononanes and tetraazaeyclododecanes, with dihydroxyphosphorylmethyl or dihydroxyphosphorylethyl groups attached to some, but not all, of the nitrogen atoms, these groups optionally substituted at the methyl or ethyl bridges with alkyl, aryl, hydroxyl or amino groups. Moreover, paramagnetic complexes of amine ligands containing a combination of phosphonate groups and other groups joined to the nitrogen atoms represent a heretofore unrecognized group of contrast agents fully suitable for use as general contrast enhancement agents.

DETAILED DESCRIPTION OF THE INVENTION AND PREFERRED EMBODIMENTS

Among the ligands used in the practice of the present invention are the embodiments represented by the following formulas:

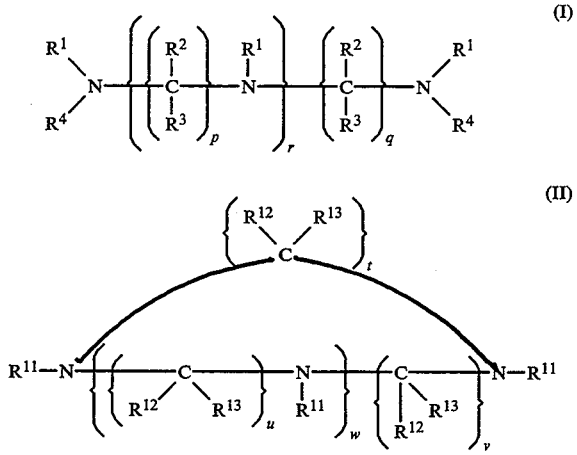

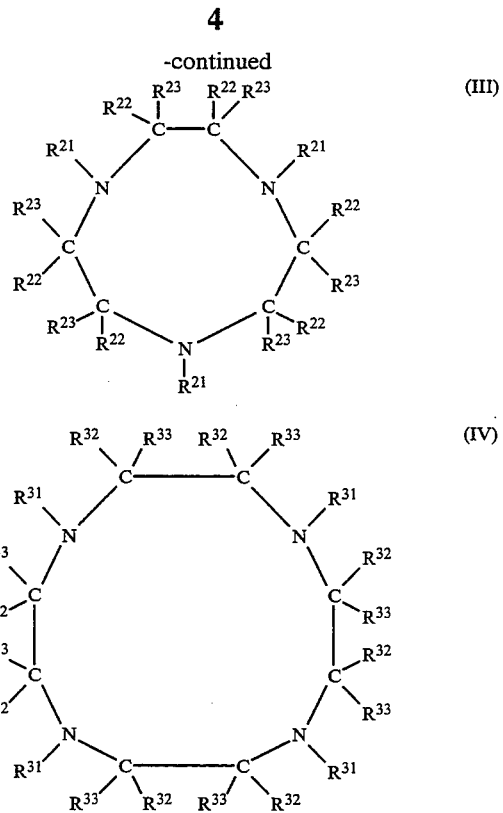

The $R^1$, $R^4$, $R^{11}$, $R^{21}$ and $R^{31}$ groups in these formulas are defined such that at least two of these groups on any single molecule are phosphonate groups which may be the same or different on any particular species, and any remaining $R^1$, $R^4$, $R^{11}$, $R^{21}$ or $R^{31}$ groups are nonphosphonate groups, which may likewise be the same or different on any particular species. The phosphonate groups are represented by

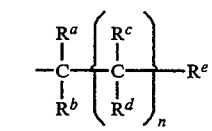

in which:

$R^a$, $R^b$ and $R^c$ are independently H, or alkyl or aryl groups which do not interfere with complexation;

$R^d$ is H, OH, NH$_2$, or alkyl or aryl groups which do not interfere with complexation; and n is zero or 1.

The nonphosphonate groups are either H, or alkyl or aryl groups which do not interfere with complexation, or are groups represented by the formula

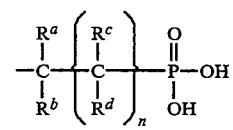

in which:

$R^a$, $R^b$, $R^c$, $R^d$ and n are as defined above, and $R^e$ is either a carboxyl group (—CO$_2$H), a 2-hydroxy phenyl group, optionally bearing additional ring substituents at the 3-6 positions, or a hydroxyl-bearing group of the formula

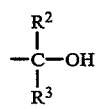

in which $R^2$ and $R^3$ are as defined below.

In this definition of $R^1$, $R^4$, $R^{11}$, $R^{21}$, and $R^{31}$, certain classes of compounds are preferred. For those species in which n is 1, one preferred class is that in which $R^a$, $R^b$ and $R^c$ are each H; and $R^d$ is H, OH, $NH_2$, $C_1$-$C_8$ alkyl, phenyl or benzyl. Another preferred class is that in which $R^a$, $R^b$ and $R^c$ are each H; and $R^d$ is H, OH, $NH_2$, $C_1$-$C_4$ alkyl or benzyl. For those species in which n is zero, a preferred class is that in which $R^a$ and $R^b$ are independently H, $C_1$-$C_4$ alkyl or benzyl, while another preferred class is that in which $R^a$ and $R^b$ are independently H, $C_1C_4$ alkyl or benzyl, and still another preferred class is that in which $R^a$ is H and $R^b$ is H, $C_1$-$C_4$ alkyl or benzyl.

The two $R^4$ groups in Formula I may alternatively be joined together as a single rivalent group bridging the two end nitrogen atoms and having the formula

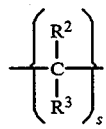

in which $R^2$ and $R^3$ are as defined below, and s is at least 2, preferably 2 or 3.

The $R^2$, $R^{12}$, $R^{22}$ and $R^{32}$ groups in these formulas may also be the same or different on any single species, and are each independently H or alkyl, aryl or mixed alkyl aryl groups (such as alkyl aryl ethers) which do not interfere with complexation.

Similarly, the $R^3$, $R^{13}$, $R^{23}$ and $R^{33}$ groups in these formulas may also be the same or different on any single species, and are each independently H or alkyl, aryl or mixed alkyl aryl groups (such as alkyl aryl ethers) which do not interfere with complexation.

In Formula I, the subscripts p and q may be the same or different, and are each either 2 or 3. The subscript r is 1, 2 or 3, preferably 1 or 2.

In Formula II, t, u and v may be the same or different, and are each either 2 or 3. The value of w is at least 1, more preferably 1 to 4 inclusive, still more preferably 1 to 3 inclusive, and most preferably either 1 or 2.

The complexation referred to in the descriptions of the alkyl and aryl groups is the complexation of the ligand with a paramagnetic metal cation to form a thelate. Alkyl and aryl groups which do not interfere with such complexation extend to a wide range in terms of size and configuration. Preferred alkyl groups are those having 1 to 8 carbon atoms, with 1 to 4 carbon atom alkyls more preferred, and methyl and ethyl the most preferred. Both straight-chain and branched-chain alkyls are included. Preferred aryl groups are benzyl and phenyl, particularly benzyl.

Paramagnetic metals of a wide range are suitable for complexation with these ligands in the formation of the contrast enhancement agents of the present invention. These metals tend to focus in elements having atomic numbers of 22-29 (inclusive), 42, 44 and 58-70 (inclusive), and have oxidations states of 2 or 3. Of these, the ones having and atomic number of 22-29 (inclusive) and 58-70 (inclusive) are preferred, and those having atomic numbers of 24-29 (inclusive) and 64-68 (inclusive) are more preferred. Examples of such metals are chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III). Chromium (III), manganese (II), iron (III) and gadolinium (III) are particularly preferred, with iron (III) the most preferred.

Physiologically or pharmacologically compatible salts of the chelates are formed by neutralizing acidic moieties on the thelate with physiologically or pharmacologically compatible cations from corresponding inorganic and organic bases and amino acids. Examples include alkali and alkaline earth metal cations, notably sodium. Further examples are primary, secondary and tertiary amines, notably, ethanolamine, diethanolamine, morpholine, glueamine, N,N-dimethylglucamine, and N-methylglucamine (commonly referred to as "meglumine"). Examples of amino acid cations are lysines, arginines and omithines. As bases, these cations may be used in the form of oxides, hydroxides, carbonates, bicarbonates or any other base forms which will release the cations.

The compounds of the present invention are capable of preparation by known procedures, some of which are described herein. The phosphonic acid, referred to herein as the "ligand," is first formed, followed by the formation of the thelate complex and then the physiologically compatible salt.

It was discovered that the procedure for combining the ligand with a paramagnetic metal cation to form the chelate complex is critical when seeking to obtain a stable, chromatographically distinct species. In particular, for most of the complexes studied it was discovered that a stable distinct species was obtained by heating a solution of the ligand and a water soluble compound of the metal cation to a temperature of at least about 50° C., preferably at least about 80° C., and more preferably to reflux (100° C. in an aqueous system), at a pH in excess of 7.0. In preferred embodiments, separation and purification are incorporated into the process of elevation of the pH and heating. Thus, after initially adding the acid form of the ligand ,and the halide form of the paramagnetic cation and heating, the pH is slowly elevated by slow addition of base in an amount of equivalents equal to the charge of the metal cation. Thus, when the metal cation is Fe(III), three equivalents are added. The neutral form of the complex can then usually be crystallized as a solid from the solvent. While heating, the crystallized solid can be added to water and sufficient base to neutralize all remaining labile protonated sites of the complex. Following formation of the chromatographically distinct complex, the neutral form of the complex can then typically be recrystallized following reacidification. The optimum temperature and base addition rate will vary from one metal ion to the next, and is readily determined by routine experimentation.

Use of the procedure described typically results in species which are stable against degradation into multiple, chromatographically distinct species over time, and upon exposure to elevated temperature. The term "chromatographically distinct" is used herein to denote species which do not indicate separation into components when subjected to suitable chromatography.

Any water soluble form of the metal may be used. Notable examples are halide salts. Chlorides are particularly preferred. Sparingly water soluble oxides or salts may also be used. When oxides are used, addition of base is not needed to form the neutral form of the complex.

Physiological salts are prepared from the neutral forms of the complexes by conventional procedures. In a typical procedure, the desired salt of the complex is formed from the neutral form of the complex by addition of the required equivalent of the desired base. Heating until the pH stabilizes may be required. A solid form of the salt of the complex can be obtained by conventional procedures, such as, for example, lyophilization, and the solid can be reconstituted with pharmacologically suitable aqueous solutions prior to administration to patients. The number of physiological cations present in the final product is equal to the equivalents added during the step of base addition, and is readily confirmed by independent means such as elemental analysis or potentiometric titrations.

Administration of the MRI contrast agents of the present invention to a patient or subject on whom magnetic resonance imaging is to be performed is achieved by conventional procedures known in this art and disclosed in the literature. Aqueous solutions of the agents are most conveniently used. The concentrations of the agents in these solutions and the amounts administered may vary widely, the optimum in each case varying with the strength of the magnetic moment of the paramagnetic metal in the agent, the contrast enhancement strength of the thelate as a whole, the method of administration, the degree of contrast enhancement desired or needed, and the age, weight and condition of the patient or subject to whom administration is made. In most cases, best results are obtained with solutions at concentrations of about 0.05 to about 2.0 moles of the paramagnetic complex per liter, preferably about 0.1 to about 1.0 mole per liter. Likewise, best results in most cases are usually obtained with dosages ranging from about 0.01 to about 1.0 millimole of agent per kilogram of whole body weight (mM/kg), preferably from about 0.05 to about 0.5 mM/kg. Administration may be achieved by any parenteral route and method, most notably by intravenous administration. The rate of administration may likewise vary, best results generally being obtained at rates ranging from about 0.1 mM/min/kg to about 1.0 mM/sec/kg.

The following examples are offered for purposes of illustration, and are intended neither to define nor limit the invention in any manner.

EXAMPLE I

SYNTHESES OF LIGANDS

This example illustrates the preparation of compounds where two or more, but not all, of the pendant arms of the ligands are phosphonate groups and typically the remaining pendant arms are nonphosphonate oxygen donor groups. Species based on both 1,4,7-triazacyclononane and 1,4,7,10-tetraazacyclododecane are illustrated in parallel fashion.

A. Synthesis of N,N'-Bis(dihydroxyphosphorylmethyl)-1,4,7-triazacyclononane

To 2.0 millimoles of N-tosyl-1,4,7-triazacyclononane dihydrobromide was added 4.0 millimoles of formaldehyde (37% in water), and the mixture was reacted for fifteen minutes at room temperature. Four millimoles of diethylphosphite were then added and the mixture reacted at room temperature for thirty minutes. Water and excess sodium bicarbonate were added and the product was extracted into ethyl acetate. Following evaporation of the ethyl acetate, the product was purified by passage through a silica column employing 5% methanol in chloroform as the eluant. The identity of the product as N-tosyl-N',N''-bis(diethylphosphorylmethyl)-1,4,7-triazacyclononane was confirmed by proton NMR.

The reaction was then repeated employing larger quantities of reactants. Seven millimoles of the product thus obtained was placed in a mixture consisting of 32 mL of 40% HBr and 18 mL of acetic acid, and the reaction refluxed for 24 hours. The reaction mixture was then evaporated to dryness, and the residue was dissolved in water which was extracted twice with ether to remove contaminants. The water fraction was clarified with charcoal, and its pH was elevated to 2.0 to 4.5 by addition of NaOH. A white solid precipitated from the solution. The identity of the solid after filtration was confirmed by NMR as N',N''-bis(dihydroxyphosphorylmethyl)-1,4,7-triazacyclononane.

B. Synthesis of N-Carboxymethyl-N',N'',-bis(dihydroxyphosphorylmethyl)-1,4,7-triazacyclononane To a solution of 0.25 millimoles of N,N'-bis(dihydroxyphosphorylmethyl)-1,4,7-triazacyclononane in water were added 0.3 millimoles of chloroacetic acid, and the pH was adjusted to 9.0 by dropwise, addition of NaOH. The mixture was then heated to 80° C. and held at that temperature overnight. Hydrochloric acid was then added to a pH of 1.5, and the water was evaporated. The solids were then triturated with ether followed by ethanol to remove contaminants, and the remaining solid product was identified by proton NMR as N-carboxymethyl-N',N''-bis(dihydroxyphosphorylmethyl)-1,4,7-triazacyclononane.

C. Synthesis of N,N'-Bis(carboxymethyl)-N'',N'''-bis(dihydroxyphosphorylmethyl)-1,4,7,10-tetraazacyclododecane To 5.0 millimoles of 1,4,7,10-tetraazacyclododecane was added 10 millimoles of formaldehyde (37% in water) followed by slow addition of 10 millimoles of diethylphosphite. The reaction mixture was allowed to stand at room temperature for two hours. Water was then added and the product was extracted into chloroform and purified by chromatography using SiO$_2$ with 5% methanol in chloroform as eluant. The identity of the product was confirmed by proton NMR as N,N'-bis(diethylphosphorylmethyl)-1,4,7,10-tetraazacyclododecane.

One millimole of the product was dissolved in methanol, and 2.4 millimoles of bromoethylacetate and excess potassium carbonate were added. The resulting mixture was heated to 60° C. and held at that temperature overnight. Water was then added to the reaction mixture, and the product was extracted into chloroform, then purified by chromatography through SiO$_2$ using: 10% methanol in chloroform as eluant. The identity of the product was confirmed by NMR as N,N'-bis(diethylphosphorylmethyl)-N'',N'''-bis(carboxymethyl ethyl ester)-1,4,7,10-tetraazacyclododecane.

The ethyl ester groups of this product were removed by hydrolysis, by dissolving the compounds in concentrated HCl and heating to 80° C. for 6-8 hours. The hydrochloric acid was then removed by evaporation, leaving N,N'-bis(carboxymethyl)-N'',N'''-bis(dihydroxyphosphorylmethyl)-1,4,7,10-tetraazacyclododecane as the final product, whose identity was then confirmed by proton NMR.

D. Synthesis of N-Carboxymethyl-N',N'',N'''-tris(dihydroxyphosphorylmethyl)-1,4,7,10-tetraazacyclododecane N,N',N''-Tris(diethylphosphorylmethyl)-1,4,7,10-tetraazacyclododecane was synthesized in a fashion identical to that used in the synthesis of N,N'-bis(diethylphosphorylmethyl)-1,4,7,10-tetraazacyclododecane in Part C of this example, but with the use of 15 millimoles of formaldehyde and 15 millimoles of diethylphosphite. 1.5 millimoles of the N,N',N''-tris(diethylphosphorylmethyl)-1,4,7,10-tetraazacyclododecane product was dissolved in methanol and 2 millimoles of bromoethylacetate and excess potassium carbonate were added. The resulting mixture was refluxed for 20 hours. The methanol was then evaporated from the mixture and the residue dissolved in water. The product was then extracted from the water into chloroform. The identity of the product was confirmed by proton NMR as N-(carboxymethyl, ethyl ester)-N',N'',N'''-tris(diethyl-phosphorylmethyl)-1,4,7,10-tetraazacyclododecane. This compound was dissolved in concentrated hydrochloric acid and heated to 80° C. for six to eight hours. The resulting solution was evaporated to dryness to remove excess HCl. The remaining solids were identified by proton NMR as N-carboxymethyl-N',N'',N'''-tris(dihydroxyphosphoryl-methyl)-1,4,7,10-tetraazacyclododecane.

E. Synthesis of N-(2-Hydroxypropyl)-N',N'',N'''-tris(dihydroxyphosphorylmethyl)-1,4,7,10-tetraazacyclododecane To 5 millimoles of 1,4,7,10-tetraazacyclododecane and 15 millimoles of formaldehyde (37% in water) were slowly added 15 millimoles of diethylphosphite. After reaction for two hours at room temperature, water was added and the product was extracted into chloroform. The product was purified by chromatography using SiO$_2$ with 5% methanol in chloroform as eluant. The identity of the product was then confirmed by proton NMR as N',N'',N'''-tris(diethylphosphorylmethyl)-1,4,7,10-tetraazacyclododecane.

One millimole of this product was dissolved in methanol, and an excess of propylene oxide was added. After reaction for 5 hours at room temperature, the methanol and excess propylene oxide were removed by evaporation. The product thus obtained was confirmed by NMR as N-(2-hydroxypropyl)-N',N'',N'''-tris(diethylphosphorylmethyl)-1,4,7,10-tetraazacyclododecane.

The ethyl ester groups of this product were removed by hydrolysis using HCl as described in Part C of Example 1 above. The HCl was then removed by evaporation, the pH adjusted to 2.0-3.0 with NaOH, and the solids triturated with ethanol. The final product was confirmed as N-(2-hydroxypropyl)-N',N'',N'''-tris-(dihydroxyphosphorylmethyl)-1,4,7,10-tetraazacyclododecane by NMR.

Those skilled in the art will recognize that the procedures described above can be employed in analogous manner to synthesize similar compounds having a mixture of phosphonate groups and other oxygen-containing donor sets as ligand arms of the subject ligands.

EXAMPLE II

PREPARATION OF METAL CATION COMPLEXES

A. Fe(III) Complex of N,N'-Bis(dihydroxyphosphorylmethyl)-1,4,7-triazacyclononane The ligand N,N'-bis(dihydroxyphosphorylmethyl)-1,4,7-triazacyclononane was added to an excess of FeCl$_3$ in water. The pH was adjusted to neutrality employing sodium hydroxide. A chromatographically distinct product was formed which had an R$_f$ of between 0.1 and 0.2 on thin layer chromatography run on a silica plate which was developed employing 1:1 methanol:phosphate buffer at pH=7.0.

B. Fe(III) Complex of N-Carboxymethyl-N',N''-bis(dihydroxyphosphorylmethyl)-1,4,7-triazacyclononane The ligand N-carboxymethyl-N',N''-bis(dihydroxyphosphorylmethyl)-1,4,7-triazacyclononane was reacted with excess FeCl$_3$ in water. The pH was adjusted to neutrality employing sodium hydroxide. A chromatogaphically distinct product was formed which had an R$_f$ of between 0.3 and 0.4 on thin layer chromatography run on a silica plate which was developed employing 1:1 methanol:phosphonate buffer at pH=7.0 to which tetraethyl ammonium chloride had been added.

EXAMPLE III

IN VIVO DISTRIBUTION AND WHOLE BODY CLEARANCE STUDIES

A radioisotopically labeled analogue of the complex described in Part B of Example II was prepared by use of Fe(III) (iron-59) and N-carboxymethyl-N',N''-bis(-dihydroxy-phosphorylmethyl)-1,4,7-trazacyclononane, employing the procedure described in Part B of Example II. The radioisotopically labeled complex thus prepared was subjected to radiochromatographic purification employing a silica substrate developed with 1:1 methanol:phosphate buffer at pH=7.0. The purified radiolabeled complex was qualified employing radiochromatography to insure acceptable radiopurity and identity with the complex.

The radioisotopically labeled complex was then administered intravenously to mice in order to measure the in vivo distribution and whole body clearance. The location of the test species in the mice's bodies and the rate at which the test species were cleared from the, mice's bodies after administration were determined by radioassay of tissues obtained at necropsy and whole body counting, both performed using conventional gamma ray counting techniques. These measurements indicated that, within one hour following administration of the radiolabeled complex, the concentration of the complex in bone was substantially greater than that in whole blood and the concentration in bone which had previously been fractured was substantially higher than that in normal bone. The measurements further indicated that, within 24 hours following administration of the complex, over 95% of the complex had been excreted from the body.

The foregoing is offered primarily for purposes of illustration. It will be readily apparent to those skilled in the art that further variations, substitutions and modifications in the substances and procedures involved in the invention beyond those specifically disclosed herein may be made without departing from the spirit and scope of the invention.

What is claimed is:

1. A method of preferentially enhancing magnetic resonance image contrast, said method comprising administering to said patient an effective amount of a pharmaceutical agent comprising a physiologically compatible salt of the complex produced by the addition of a suitable paramagnetic metal cation to a chelator having the formula

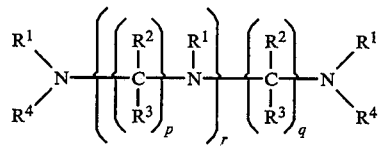

in which:
  p is 2 or 3;
  q is 2 or 3;
  r is 2 or 3;
  at least three but not all of the $R^1$ moieties are independently phosphonate-bearing groups of the formula

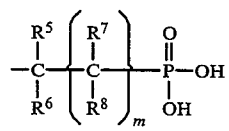

in which $R^5$, $R^6$ and $R^7$ are independently selected from the group consisting of H and alkyl and aryl groups which do not interfere with complexation; $R^8$ is selected from the group consisting of H, OH, $NH_2$, and alkyl and aryl groups which do not interfere with complexation; and m is zero or 1;
  the $R^1$ moieties which are not phosphonate-bearing groups are members independently selected from the group consisting of H, alkyl and aryl groups which do not interfere with complexation, and groups of the formula

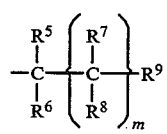

in which $R^5$, $R^6$, $R^7$, $R^8$ and m are as defined above, and $R^9$ is a member selected from the group consisting of carboxyl, 2-hydroxy phenyl, and

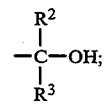

the $R^2$ moieties are each independently selected from the group consisting of H and alkyl and aryl groups which do not interfere with complexation;
the $R^3$ moieties are each independently selected from the group consisting of H and alkyl and aryl groups which do not interfere with complexation; and
the $R^4$ moieties together form a single divalent group having the formula

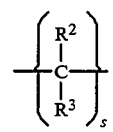

in which $R^2$ and $R^3$ are as defined above, and s is at least 2.

2. A method in accordance with claim 1 in which s is 2 or 3.

3. A method of preferentially enhancing magnetic resonance image contrast in bone tissue and other tissue of a patient bearing recognition features in common with bone tissue, said method comprising administering to said patient an effective amount of a pharmaceutical agent comprising a physiologically compatible salt of the complex produced by the addition of a suitable paramagnetic metal cation to a chelator having the formula

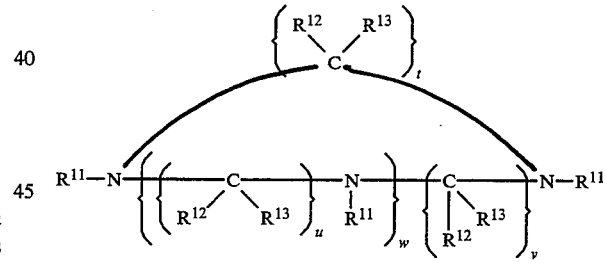

in which:
  t is 2 or 3;
  u is 2 or 3;
  v is 2 or 3;
  w is at least 2;
  at least two but not all of the $R^{11}$ moieties are independently phosphonate-bearing groups of the formula

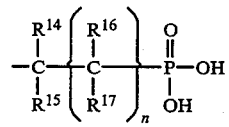

in which $R^{14}$, $R^{15}$ and $R^{16}$ are independently selected from the group consisting of H and alkyl and aryl groups which do not interfere with complexation; $R^{17}$ is selected from the group consisting of H, OH, $NH_2$, and alkyl and aryl groups which do not interfere with complexation; and n is zero or 1;

the $R^{11}$ moieties which are not phosphonate-bearing groups are members independently selected from the group consisting of H, alkyl and aryl groups which do not interfere with complexation, and groups of the formula

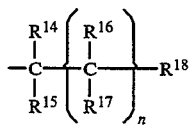

in which $R^{14}$, $R^{15}$, $R^{16}$, $R^{17}$, and n are as defined above, and $R^{18}$ is a member
selected from the group consisting of carboxyl, 2-hydroxy phenyl, and

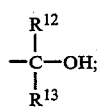

the $R^{12}$ moieties are each independently selected from the group consisting of H and alkyl and aryl groups which do not interfere with complexation; and
the $R^{13}$ moieties are each independently selected from the group consisting of H and alkyl and aryl groups which do not interfere with complexation.

4. A method in accordance with claim 3 in which $R^{14}$, $R^{15}$ and $R^{16}$ are independently selected from the group consisting of H, $C_1$-$C_8$ alkyl, phenyl and benzyl; and $R^{17}$ is selected from the group consisting of H, OH, $NH_2$, $C_1$-$C_8$ alkyl, phenyl and benzyl.

5. A method in accordance with claim 3 in which $R^{14}$, $R^{15}$ and $R^{16}$ are independently selected from the group consisting of H, $C_1$-$C_4$ alkyl and benzyl; and $R^{17}$ is selected from the group consisting of H, OH, $NH_2$, $C_1$-$C_4$ alkyl and benzyl.

6. A method in accordance with claim 3 in which $R^{14}$, $R^{15}$ and $R^{16}$ are each H; $R^{17}$ is selected from the group consisting of H, OH, $NH_2$, $C_1$-$C_8$ alkyl, phenyl and benzyl; and n is 1.

7. A method in accordance with claim 3 in which $R^{14}$, $R^{15}$ and $R^{16}$ are each H; $R^{17}$ is selected from the group consisting of H, OH, $NH_2$, $C_1$-$C_4$ alkyl and benzyl; and n is 1.

8. A method in accordance with claim 3 in which $R^{14}$, $R^{15}$, $R^{16}$ and $R^{17}$ are each H; and n is 1.

9. A method in accordance with claim 3 in which $R^{14}$ and $R^{15}$ are independently selected from the group consisting of H, $C_1$-$C_8$ alkyl, phenyl and benzyl; and n is zero.

10. A method in accordance with claim 3 in which $R^{14}$ and $R^{15}$ are independently selected from the group consisting of H, $C_1$-$C_4$ alkyl and benzyl; and n is zero.

11. A method in accordance with claim 3 in which $R^{14}$ and $R^{15}$ are each H; and n is zero.

12. A method in accordance with claim 3 in which the $R^{12}$ and $R^{13}$ moieties are each independently selected from the group consisting of H, $C_1$-$C_8$ alkyl, phenyl and benzyl.

13. A method in accordance with claim 3 in which the $R^{12}$ and $R^{13}$ moieties are each independently selected from the group consisting of H, $C_1$-$C_4$ alkyl and benzyl.

14. A method in accordance with claim 3 in which the $R^{12}$ moieties are each H; and the $R^{13}$ moieties are each independently selected from the group consisting of H, $C_1$-$C_8$ alkyl, phenyl and benzyl.

15. A method in accordance with claim 3 in which the $R^{12}$ moieties are each H; and the $R^{13}$ moieties are each independently selected from the group consisting of H, $C_1$-$C_4$ alkyl and benzyl.

16. A method in accordance with claim 3 in which the $R^{12}$ moieties are each H; and the $R^{13}$ moieties are each independently selected from the group consisting of H and $C_1$-$C_4$ alkyl.

17. A method in accordance with claim 3 in which the $R^{12}$ moieties are each H; and the $R^{13}$ moieties are each independently selected from the group consisting of H and methyl.

18. A method in accordance with claim 3 in which the $R^{12}$ moieties are each H; and the $R^{13}$ moieties are each H.

19. A method in accordance with claim 3 in which t, u and v are each 2.

20. A method in accordance with claim 3 in which w is 2 to 4.

21. A method in accordance with claim 3 in which w is 2 to 3.

22. A method in accordance with claim 3 in which w is 2.

23. A method in accordance with claim 3 in which said paramagnetic metal cation is a cation of an element having an atomic number of 22 to 29 or 58 to 70.

24. A method in accordance with claim 3 in which said paramagnetic metal cation is a cation of an element selected from the group consisting of chromium, manganese, iron and gadolinium.

25. A method in accordance with claim 3 in which said physiological compatible salt is comprised of said complex in combination with at least one cation selected from the group consisting of sodium and N-methylglucamine.

26. A method of preferentially enhancing magnetic resonance image contrast, said method comprising administering to said patient an effective amount of a pharmaceutical agent comprising a physiologically compatible salt of the complex produced by the addition of a suitable paramagnetic metal cation to a chelator having the formula

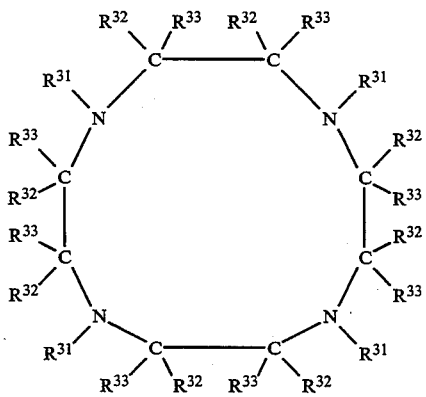

in which:
at least three but not all of the $R^{31}$ moieties are independently phosphonate-bearing groups of the formula

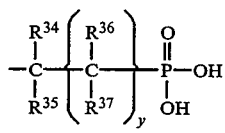

in which $R^{34}$, $R^{35}$ and $R^{36}$ are independently selected from the group consisting of H and alkyl and aryl groups which do not interfere with complexation; $R^{37}$ is selected from the group consisting of H, OH, $NH_2$, and alkyl and aryl groups which do not interfere with complexation; and y is zero or 1;

the $R^{31}$ moieties which are not phosphonate-bearing groups are members independently selected from the group consisting of H, alkyl and aryl groups which do not interfere with complexation, and groups of the formula

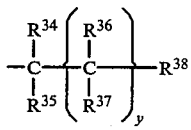

in which $R^{34}$, $R^{35}$, $R^{36}$, $R^{37}$ and y are as defined above, and $R^{38}$ is a member selected from the group consisting of carboxyl, 2-hydroxy phenyl, and

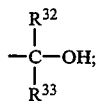

the $R^{32}$ moieties are each independently selected from the group consisting of H and alkyl and aryl groups which do not interfere with complexation; and the $R^{33}$ moieties are each independently selected from the group consisting of H and alkyl and aryl groups which do not interfere with complexation.

27. A method in accordance with claim 26 in which $R^{34}$, $R^{35}$ and $R^{36}$ are independently selected from the group consisting of H, $C_1$-$C_4$ alkyl and benzyl; and $R^{37}$ is selected from the group consisting of H, OH, $NH_2$, $C_1$-$C_4$ alkyl and benzyl.

28. A method in accordance with claim 26 in which $R^{34}$, $R^{35}$ and $R^{36}$ are each H; $R^{37}$ is selected from the group consisting of H, OH, $NH_2$, $C_1$-$C_4$ alkyl and benzyl; and y is 1.

29. A method in accordance with claim 26 in which $R^{34}$, $R^{35}$, $R^{36}$ and $R^{37}$ are each H; and y is 1.

30. A method in accordance with claim 26 in which $R^{34}$ and $R^{35}$ are independently selected from the group consisting of H, $C_1$-$C_4$ alkyl and benzyl; and y is zero.

31. A method in accordance, with claim 26 in which $R^{34}$ and $R^{35}$ are each H; and y is zero.

32. A method in accordance with claim 26 in which the $R^{32}$ and $R^{33}$ moieties are each independently selected from the group consisting of H, $C_1$-$C_4$ alkyl and benzyl.

33. A method in accordance, with claim 26 in which the $R^{32}$ moieties are each H; and the $R^{33}$ moieties are each independently selected from the group consisting of H, $C_1$-$C_4$ alkyl and benzyl.

34. A method in accordance with claim 26 in which the $R^{32}$ moieties are each H; and the $R^{33}$ moieties are each independently selected from the group consisting of H and $C_1$-$C_4$ alkyl.

35. A method in accordance with claim 26 in which the $R^{32}$ moieties are each H; and the $R^{33}$ moieties are each H..

36. A method in accordance with claim 26 in which $R^{34}$ and $R^{35}$ are each H; y is zero; the $R^{32}$ moieties are each H; and the $R^{33}$ moieties are each H.

37. A method in accordance with claim 26 in which $R^{34}$, $R^{35}$, $R^{36}$ and $R^{37}$ are each H; y is 1; the $R^{32}$ moieties are each H; and the $R^{33}$ moieties are each H.

38. A method in accordance with claim 26 in which $R^{34}$, $R^{35}$ and $R^{36}$ are each H; $R^{37}$ is OH; y is 1; the $R^{32}$ moieties are each H; and the $R^{33}$ moieties are each H.

39. A method in accordance with claim 26 in which $R^{34}$, $R^{35}$ and $R^{36}$ are each H; $R^{37}$ is $NH_2$; y is 1; the $R^{32}$ moieties are each H; and the $R^{33}$ moieties are each H.

40. A method in accordance with claim 26 in which said paramagnetic metal cation is a cation of an element having an atomic number of 22 to 29 or 58 to 70.

41. A method in accordance with claim 26 in which said paramagnetic metal cation is a cation of an element having an atomic number of 24 to 29 or 64 to 68.

42. A method in accordance with claim 26 in which said paramagnetic metal cation is a cation of an element selected from the group consisting of chromium, manganese, iron and gadolinium.

43. A method in accordance with claim 26 in which said physiological compatible salt is comprised of said complex in combination with at least one cation selected from the group consisting of sodium and N-methylglucamine.

44. A pharmaceutical agent comprising a physiologically compatible salt of a chelate of a paramagnetic metal cation and a compound having the formula

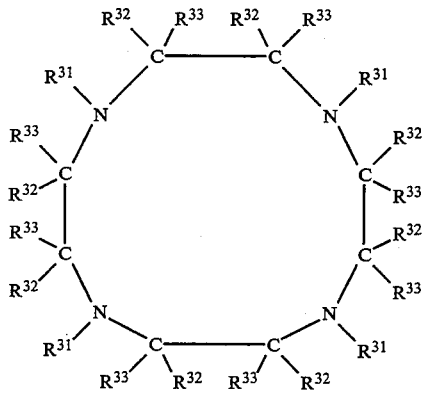

in which:
at least three but not all of the $R^{31}$ moieties are independently phosphonate-bearing groups of the formula

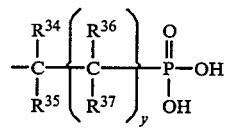

in which $R^{34}$, $R^{35}$ and $R^{36}$ are independently selected from the group consisting of H and alkyl and aryl groups which do not interfere with complexation; $R^{37}$ is selected from the group consisting of H, OH, $NH_2$, and alkyl and aryl groups which do not interfere with complexation; and y is zero or 1;

the $R^{31}$ moieties which are not phosphonate-bearing groups are members independently selected from the group consisting of H, alkyl and aryl groups which do not interfere with complexation, and groups of the formula

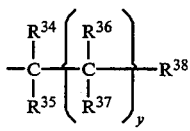

in which $R^{34}$, $R^{35}$, $R^{36}$, $R^{37}$ and y are as defined above, and $R^{38}$ is a member selected from the group consisting of carboxyl, 2-hydroxy phenyl, and

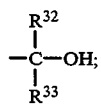

the $R^{32}$ moieties are each independently selected from the group consisting of H and alkyl and aryl groups which do not interfere with complexation; and
the $R^{33}$ moieties are each independently selected from the group consisting of H and alkyl and aryl groups which do not interfere with complexation.

45. A pharmaceutical agent in accordance with claim 44 in which $R^{34}$, $R^{35}$ and $R^{36}$ are independently selected from the group consisting of H, $C_1$-$C_8$ alkyl, phenyl and benzyl; and $R^{37}$ is selected from the group consisting of H, OH, $NH_2$, $C_1$-$C_8$ alkyl, phenyl and benzyl.

46. A pharmaceutical agent in accordance with claim 44 in which $R^{34}$, $R^{35}$ and $R^{36}$ are independently selected from the group consisting of H, $C_1$-$C_4$ alkyl and benzyl; and $R^{37}$ is selected from the group consisting of H, OH, $NH_2$, $C_1$-$C_4$ alkyl and benzyl.

47. A pharmaceutical agent in accordance with claim 44 in which $R^{34}$, $R^{35}$ and $R^{36}$ are each H; $R^{37}$ is selected from the group consisting of H, OH, $NH_2$, $C_1$-$C_8$ alkyl, phenyl and benzyl; and y is 1.

48. A pharmaceutical agent in accordance with claim 44 in which $R^{34}$, $R^{35}$ and $R^{36}$ are each H; $R^{37}$ is selected from the group consisting of H, OH, $NH_2$, $C_1$-$C_4$ alkyl and benzyl; and y is 1.

49. A pharmaceutical agent in accordance with claim 44 in which $R^{34}$, $R^{35}$, $R^{36}$ and $R^{37}$ are each H; and y is 1.

50. A pharmaceutical agent in accordance with claim 44 in which $R^{34}$ and $R^{35}$ are independently selected from the group consisting of H, $C_1$-$C_8$ alkyl, phenyl and benzyl; and y is zero.

51. A pharmaceutical agent in accordance with claim 44 in which $R^{34}$ and $R^{35}$ are independently selected from the group consisting of H, $C_1$$C_4$ alkyl and benzyl; and y is zero.

52. A pharmaceutical agent in accordance with claim 44 in which $R^{34}$ and $R^{35}$ are each H; and y is zero.

53. A pharmaceutical agent in accordance with claim 44 in which the $R^{32}$ and $R^{33}$ moieties are each independently selected from the group consisting of H, $C_1$-$C_8$ alkyl, phenyl and benzyl.

54. A pharmaceutical agent in accordance with claim 44 in which the $R^{32}$ and $R^{33}$ moieties are each independently selected from the group consisting of H, $C_1$-$C_4$ alkyl and benzyl.

55. A pharmaceutical agent in accordance with claim 44 in which the $R^{32}$ moieties are each H; and the $R^{33}$ moieties are each independently selected from the group consisting of H, $C_1$-$C_8$ alkyl, phenyl and benzyl.

56. A pharmaceutical agent in accordance with claim 44 in which the $R^{32}$ moieties are each H; and the $R^{33}$ moieties are each independently selected from the group consisting of H, $C_1$-$C_4$ alkyl and benzyl.

57. A pharmaceutical agent in accordance with claim 44 in which the $R^{32}$ moieties are each H; and the $R^{33}$ moieties are each independently selected from the group consisting of H and $C_1$-$C_4$ alkyl.

58. A pharmaceutical agent in accordance with claim 44 in which the $R^{32}$ moieties are each H; and the $R^{33}$ moieties are each independently selected from the group consisting of H and methyl.

59. A pharmaceutical agent in accordance with claim 44 in which the $R^{32}$ moieties are each H; and the $R^{33}$ moieties are each H.

60. A pharmaceutical agent in accordance with claim 44 in which $R^{34}$ and $R^{35}$ are each H; y is zero; the $R^{32}$ moieties are each H; and the $R^{33}$ moieties are each H.

61. A pharmaceutical agent in accordance with claim 44 in which $R^{34}$, $R^{35}$, $R^{36}$ and $R^{37}$ are each H; y is 1; the $R^{32}$ moieties are each H; and the $R^{33}$ moieties are each H.

62. A pharmaceutical agent in accordance with claim 44 in which $R^{34}$, $R^{35}$ and $R^{36}$ are each H; $R^{37}$ is OH; y is 1; the $R^{32}$ moieties are each H; and the $R^{33}$ moieties are each H.

63. A pharmaceutical agent in accordance with claim 44 in which $R^{34}$, $R^{35}$ and $R^{36}$ are each H; $R^{37}$ is $NH_2$; n is 1; the $R^{33}$ moieties are each H; and the $R^{33}$ m each H.

64. A pharmaceutical agent in accordance with claim 44 in which said paramagnetic metal cation is a cation of an element selected from the group consisting of chromium, manganese, iron and gadolinium.

65. A pharmaceutical agent in accordance with claim 44 in which said physiological compatible salt is comprised of said thelate in combination with at least one cation selected from the group consisting of sodium and N-methylglucamine.

* * * * *